United States Patent [19]

Falkiner

[11] Patent Number: 4,649,571
[45] Date of Patent: Mar. 17, 1987

[54] DUAL VISION WELDING HELMET

[76] Inventor: Raymond C. Falkiner, 83 Scriminger Avenue, Cambridge, Ontario, Canada, N1R 4W2

[21] Appl. No.: 671,988
[22] Filed: Nov. 16, 1984
[51] Int. Cl.[4] .............................................. A61F 9/06
[52] U.S. Cl. .............................................. 2/8; 2/432; 351/44
[58] Field of Search .......................... 2/432, 8, 9, 436; 351/44, 45

[56] References Cited

U.S. PATENT DOCUMENTS

| | | | |
|---|---|---|---|
| 1,320,931 | 11/1919 | Rutledge | 2/432 X |
| 1,386,989 | 8/1921 | Capper | 2/432 |
| 1,685,725 | 9/1928 | Rowe | 2/432 X |
| 2,187,542 | 1/1940 | Hagen | 2/8 |
| 2,362,637 | 11/1944 | Keehn | 2/8 |
| 2,545,078 | 3/1951 | Gardner | 2/432 X |
| 2,556,433 | 6/1951 | Mitchell | 2/432 |
| 2,644,160 | 7/1953 | Jacobs | 2/8 |
| 2,818,859 | 1/1958 | Peterson | 2/9 X |
| 3,141,172 | 7/1964 | Hirschmann | 2/436 |
| 3,444,561 | 5/1969 | Boyer | 2/8 |
| 3,689,136 | 9/1972 | Atamian | 2/432 X |

FOREIGN PATENT DOCUMENTS

| | | | |
|---|---|---|---|
| 2514439 | 10/1976 | Fed. Rep. of Germany | 2/432 |
| 203546 | 6/1939 | Switzerland | 2/8 |

Primary Examiner—Werner H. Schroeder
Assistant Examiner—Andrew M. Falik
Attorney, Agent, or Firm—David J. French

[57] ABSTRACT

A welding helmet is fitted with two lenses, one tinted and one relatively clear. The tinted lens is mounted forward of the eyes of the viewer and the clear lens extends obliquely away from the tinted lens towards the face of the wearer. To view the workpiece through the clear lens a wearer need only tilt the helmet without the necessity of raising his hands.

18 Claims, 5 Drawing Figures

DUAL VISION WELDING HELMET

FIELD OF THE INVENTION

This invention relates to an arc welding helmet which is provided with two lens windows for respectively viewing work pieces, both prior to and during the welding process. More particularly, this invention relates to the specific disposition of such windows within a helmet so as to permit their alternate use by a mere tipping of the head.

BACKGROUND OF THE INVENTION

In the arc welding process the welder must view his work while an arc is being drawn through a tinted lens window in his helmet. This is to protect his eyes from the brightness of the arc. Tinted windows provided for this purpose are so dark that it is not possible to satisfactorily view work through such windows when the arc is not struck. This necessitates alternate means for viewing the work prior to creation of an arc.

Typically, with single window helmets, the welder may remove or tilt back the entire helmet in order to view his work. This occupies time and may require the use of one hand.

Arrangements have been built into welding helmets to provide for the temporary opening of the tinted window either by sliding or hinged mechanisms. Such mechanisms have been operated by hand, by movement of the chin or by pressure from the welder's breath. These mechanisms are not entirely convenient to use.

It has also been proposed to provide a welding helmet with two adjacent viewing windows one with a tinted lens and one with a clear lens. For example, U.S. Pat. No. 2,362,637 to W. L. Keehn discloses two such vertically aligned window lens elements set in place of the customary single lens window of a typical helmet. To view alternately through the respective window lenses, the user of this apparatus need only tilt his head upwardly, carrying the helmet with his head, so as to align the desired window with the workpiece. To ensure that excessive light does not enter the mask through the clear lens while welding is in progress, this helmet carries an outwardly protruding visor, fixed along the line where the upper tinted lens and lower clear lens meet. While welding, this visor ensures that the lower, clear lens is shadowed from the brightness of the arc.

In another U.S. Pat. No. 2,644,160 to J. H. Jacobs, a similar arrangement is adopted, except that the clear lens is mounted above and rearwardly from the tinted lens. According to this patent, the user must tilt his head downwardly, in order to view his work through the clear window. By offsetting the clear lens rearwardly of the tinted lens, this helmet relies on the frame around the tinted lens to serve the function of the visor in the Keehn patent.

Both of these prior art patents rely upon opaque visor-like surfaces to shadow the clear lens window of the mark from the brightness of the art. The presence of a visor intermediate the viewing lines between the respective windows forces the user to tilt his head to a greater degree when switching his view between such windows. Thus the fields of view through such windows are not virtually contiguous. Additionally, the field of view, in both cases, is limited by the presence of the visor element.

Furthermore, in both such masks the lenses are mounted relatively close to the user's face and are therefore liable to collect condensation arising from moisture present due to sweat or exhaled breath. This can obscure vision and create discomfort.

OBJECTS OF THE INVENTION

It is accordingly one object of the invention herein to provide an alternate, more convenient, configuration for the placement of clear and tinted viewing windows in a welding mask that may be used by a wearer merely by tipping the head.

A further object of the invention is to reduce the tendency of viewing windows on a welding mask to fog-up in use and for moisture from the breath of the user to accumulate within the mask.

SUMMARY OF THE INVENTION

According to this invention in its broadest aspect a welding mask adapted for use by a wearer is provided with two viewing windows, one of which contains a tinted lens and the other a lens which is relatively transparent. The tinted lens is displaced outwardly from the face of the user. The window for the relatively transparent lens extends at an angle rearwardly away from the plane of the tinted lens.

By a further feature of the invention the tinted lens is mounted in a plane which is approximately perpendicular to the normal line of vision through such window.

By a further feature of the invention the relatively transparent lens extends rearwardly from the vicinity of a bordering edge of the tinted lens. By a further feature the edge of the relatively transparent lens is sufficiently proximate to the edge of the tinted window to provide a field of vision therethrough which is virtually contiguous to that through the tinted lens.

In a more particular aspect of the invention, the inner edge of the window adapted to receive the relatively transparent lense terminates along a line proximate to the limit of the field of vision of a wearer whose eyes are upwardly or downwardly inclined.

By a further aspect of the invention the relatively transparent lens is partially mirrored so as to enhance its reflectivity when viewed from the exterior of the mask, but not so mirrored as to prevent viewing therethrough from the interior side of the mask under normal lighting conditions.

By a further aspect of the invention the mark is provided with an interior enlarged region within the mask between the eyes of a user and the viewing windows which region is adapted to permit the circulation of air therewithin.

By a further aspect of the invention, the mask incorporates a form fitting lining adapted to lie sealingly against the cheeks and nose of the wearer and reduce the tendency for exhaled breath of the user to enter the enlarged interior region of the mask between the eyes of a user and the viewing windows.

These and further features of the invention will become apparent from the description of the preferred embodiment set forth below.

DESCRIPTION OF THE PREFERRED EMBODIMENT

Figure 1:
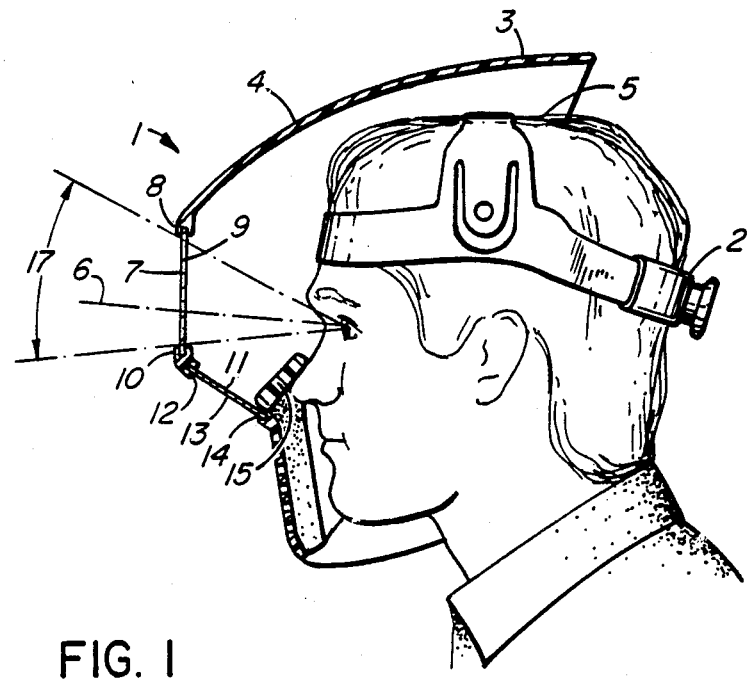
FIG. 1 is a cross-sectional view through a mask incorporating the two viewing windows and the outline of a wearer viewing through the upper window.

In FIG. 1 a mask 1 is provided with a supporting head band 2 of conventional design. The mask 1 is provided with an upper head-covering region 3 and an upper, forward projecting region 4 that extends outwardly from the forehead of a wearer 5 by approximately 2-3 inches.

Centered approximately with the forward line of vision 6 of the wearer and mounted perpendicularly thereto is a tinted lens 7 set in a window frame 8 at the front of the mask 1. Together the window frame 8 and lens 7 constituted a tinted window 9. The boundaries of the tinted window 9 define the limits of the field of vision 17, available to a wearer 5, therethrough.

Beneath the lower edge 10 of the frame 8 of the tinted window 9 and extending at an angle downwardly and towards the face of the wearer 5 from the lower edge 10 of the frame 8 is a relatively transparent lens 11. This lens is mounted in its own frame 12 and together these elements comprise the clear window 13.

Figure 2:
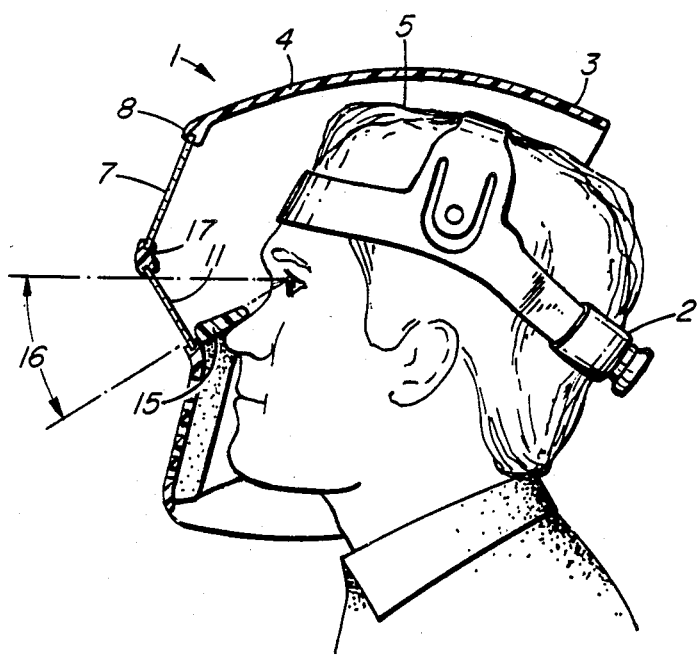
FIG. 2 is a cross-sectional view as in FIG. 1 with the outline of a wearer viewing through the lower window.

The lower edge 14 of the clear window 13 terminates along a line 17 in the vicinity of the limit of the field of vision of a wearer 5 whose eyes are downwardly inclined over his nose and cheeks as in FIG. 2. In the preferred embodiment as depicted, this lower edge 14 is formed along a lining 15 of rubbery sponge material, which is, in turn, form-fitted over the cheeks and nose of the wearer 5.

In FIG. 2, the field of vision 16 of the wearer 5 through the transparent lens 11 is shown. Except for the thicknesses of the lower edge 10 of the tinted window frame 8, and the upper edge 16 of the transparent lens frame 12, the field of view 16 of a wearer 5 through the transparent lens is virtually contiguous to the field of view 17 through the tinted window 9.

When the wearer 5 is welding his line of vision will be through the tinted window 9. Viewed, as in FIG. 3, from the workpiece on which an arc is being struck, the relatively transparent lens 11, in this configuration, presents a reduced surface area for intercepting light radiating from the arc. This is due to the angle of inclination of the relatively transparent lens 11 with respect to the direction of the light. This angle of inclination also results in some reflectance of arc light from the relatively transparent lens 11, reducing the illumination of the interior of the mask 1 through this lens. This reflectance can be enhanced by partially mirroring either the outer or interior surface of this lens or by installing the semi-reflective splash guard lens. Alternately, a semi-reflective film, such as that produced in the United States by Vanleer Plastics under the brand name "Valvac" may be placed over this lens on either the interior or exterior surfaces to enhance reflectivity. Some absorption may also occur in the relatively transparent lens 11. This absorption is higher when light is transmitted through this lens obliquely, further reducing excessive illumination of the interior of the mark.

When the arc is extinguished, the wearer may view the workpiece through the clear window 13 by rotating the mask 1 through a simple upwards tilt of the head. The area of the clear window 13 presented to the workpiece under such conditions is apparent from FIG. 4. While the relatively clear lens 11 is not perpendicular to the line of vision in this configuration, the workpiece may be readily viewed through the clear window 13, obliquely.

Figure 5:
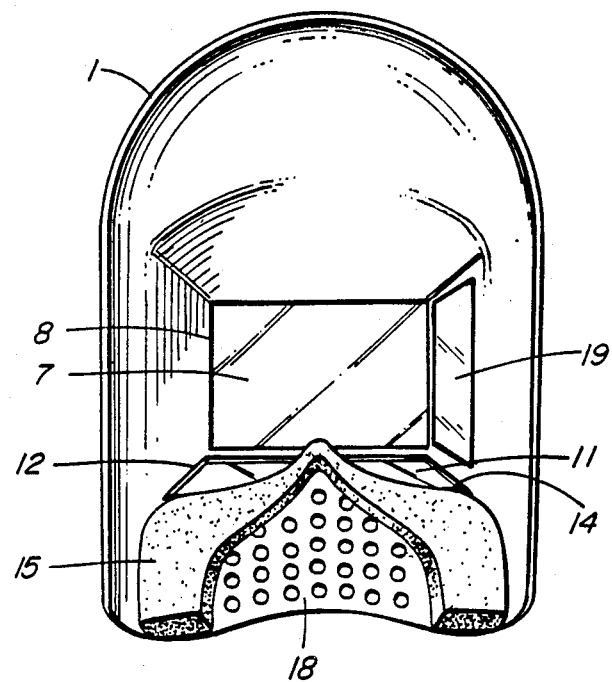
FIG. 5 is a rear view of the mask showing both windows and a form-fitting lining.

Within the interior of the mask, as depicted in FIG. 5, the cavity formed by the forward disposition of the tinted window 9 creates a space within which air may circulate. To enhance the circulation of fresh air within the mask, vents or louvres (not shown) may be incorporated into the side panels and top 4 of the mask 1. This circulation will tend to reduce condensation on the lenses arising from sweating by the wearer.

The lining 15, which receives the lower edge 10 of the clear window 13 is depicted as well in FIG. 5. By forming a relatively tight seal along the cheeks and over the nose of a user, exhaled breath will tend to flow downwardly and be excluded from the interior of the mark 1. To further enhance the departure of moisture laden breath, an air permeable, but spark excluding, screen 18 may be placed in the mask 1 below the lining 15.

Figure 3:
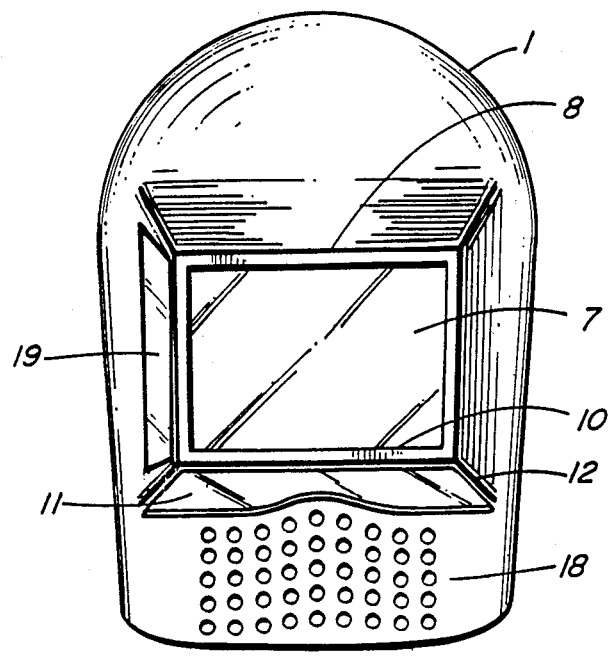
FIG. 3 is a front view of the mask of FIG. 1 along the line of sight through the tinted window.
Figure 4:
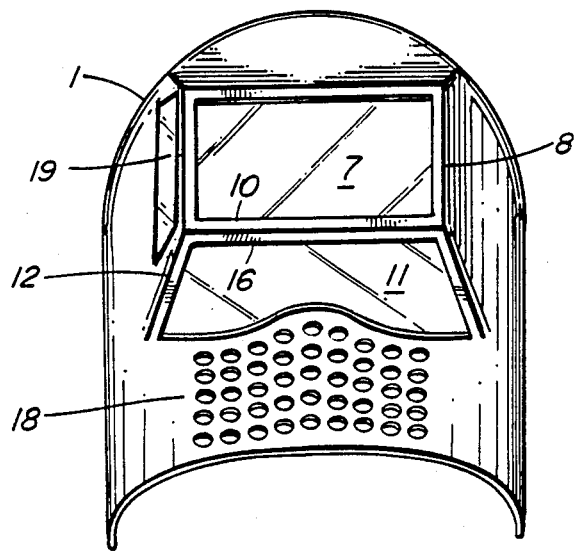
FIG. 4 is a partially rotated front view of the mask of FIG. 1 along the line of sight through the relatively transparent lens.

In the preferred embodiment the clear window 13 is shown as being mounted below the tinted window 9. This may be interchanged by placing the clear window 13 on the top or sides. In the first such case, the clear window 13 would extend backwardly and upwardly towards the forehead of the wearer. An upwardly mounted clear window may be preferrable when working on polished or bright metal, such as aluminum, which is located below the point of welding and brightly reflects light from the arc. Side windows may be desirable where the welder would benefit from improved peripheral vision. An example of such an additional transparent lens is shown in FIGS. 3, 4 and 5. A side lens 19 is shown mounted in the right hand side of the mask 1. The forward edge 20 of the side lens 19 is optionally located adjacent to the window frame 8 carrying the tinted lens 7. This additional side lens may, for maximum visibility, extend back to the limit of the direct line of sideways vision of a wearer 5.

Whether the clear window is mounted on the bottom, a side, or on the top, it should be inclined away from the tinted window towards the face of the wearer. In all cases where the tinted lens is mounted approximately perpendicular to the normal line of vision therethrough, the preferred included angle between the planes of the clear and tinted windows is 115°-120°.

The tinted lens 7 is shown as being mounted approximately perpendicularly to the line of vision 6 of the wearer therethrough. This is not essential. This lens may also be mounted so as to be viewed through obliquely.

The relatively transparent lens 11 is shown as extending backwardly from a bordering edge 10 of the window carrying the relatively tinted lens 7. While this is desirable, it is not essential. The relatively transparent lens 11 may also be mounted along a plane intersecting the surface of the tinted lens 7, or an extension thereof.

A mask may also be constructed incorporating more than one clear window, mounted above and below the tinted window or mounted on the sides of the forward extension of the mask 1. By maximizing the ambient light permitted to enter the mask 1 through such windows, the tendency of the pupils of the eyes of a wearer to dilate will be reduced. This will, in turn, reduce the shock to the eyes when the arc is struck. For this same reason, it is desirable to maximize the area of the clear window.

The foregoing description is of a preferred embodiment of the invention. The invention in its broadest and more particular aspects is defined in the claims which follow.

I claim:

1. A welding mask adapted to be worn by a wearer, comprising a face protecting mask which shields the entire face, having first and second viewing windows, the first of said windows incorporating a tinted lens adapted for viewing under welding conditions and said second window incorporating a relatively transparent lens adapted for viewing work to be welded prior to striking an arc or lighting a torch, wherein said tinted lens is mounted forward of the face of the wearer and said relatively transparent lens extends at an angle rearwardly towards the wearer away from the plane of the tinted lens and at an acute angle to the normal line of vision of the wearer through said tinted lens, said angle being sufficient to substantially reduce the amount of light entering into the mask through said second viewing window when the wearer is viewing a light source, located at arm's length along the normal line of vision through said first viewing window.

2. A welding mask as in claim 1 wherein the tinted lens is mounted in a plane which is approximately perpendicular to the normal line of vision through the said tinted lens.

3. A welding mask as in claim 2 wherein the relatively transparent lens extends rearwardly towards the face of the wearer away from the vicinity of a bordering edge of the window incorporating said tinted lens.

4. A welding mask as in claim 3 wherein the forward edge of the relatively transparent lens is sufficiently proximate to the edge of the tinted lens to provide a field of vision through said relatively transparent lens which is virtually contiguous to the field of vision through the tinted lens.

5. A welding mask as in claims 2, 3 or 4 wherein the included angle between the planes of said tinted lens and said relatively clear lens opening in the direction towards said wearer is in the range of 115°-120°.

6. A welding mask as in claim 1 wherein the relatively transparent lens has an inner edge which terminates along a line proximate to the limit of the field of vision of a wearer whose eyes are downwardly or laterally inclined.

7. A welding mask as in claim 1 wherein partial mirroring means is incorporated in or adjacent to said relatively transparent lens so as to enhance the reflection of light approaching said lens from the exterior of said mask, while permitting viewing through said lens from the interior of said mask under normal lighting conditions.

8. A welding mask as in claims 4, 6 or 7 in which said relatively transparent lens is mounted beneath said tinted lens.

9. A welding mask as in claims 4, 6 or 7 adapted for viewing work to be welded, prior to striking an arc, or lighting a torch, in which one or more additional relatively transparent lenses are mounted adjacent to the bordering edges of the window incorporating said tinted lens, wherein said additional lenses are all angled rearwardly away from the plane of the tinted lens and towards the wearer at an acute angle to the normal line of vision of the wearer through said tinted lens, said angle being sufficient to substantially reduce the amount of light entering into said mask through said second viewing window when the wearer is viewing a light source, located at arm's length along the normal line of vision through said first viewing window.

10. A welding mask as in claim 1 wherein said tinted lens and said relatively transparent lens provide part of the boundaries of an enlarged interior region within said mask between the eyes of a wearer and said lens, whereby air may circulate within said region.

11. A welding mask as in claims 6, 7 or 10 wherein the included angle between the plates of said tinted lens and said relatively clear lens opening in the direction towards said wearer is in the range of 115°-120°.

12. A welding mask as in claim 10 wherein air circulation vents are provided which permit the circulation of outside air within said interior region.

13. A welding mask as in claim 10 incorporating a form fitting lining adapted to lie sealingly against the cheeks and nose of the wearer and reduce the tendancy for exhaled breath of the wearer to enter the enlarged interior region within said mask.

14. A welding mask as in claims 10, 12 or 13 in which said relatively transparent lens is mounted beneath said tinted lens.

15. A welding mask as in claims 10, 12 or 13 adapted for viewing work to be welded, prior to striking an arc or lighting a torch, in which one or more additional relatively transparent lenses are mounted adjacent to the bordering edges of the window incorporating said tinted lens, wherein said additional lenses are all angled rearwardly away from the plane of the tinted lens and towards the wearer at an acute angle to the normal line of vision of the wearer through said tinted lens, said angle being sufficient to substantially reduce the amount of light entering into said mask through said second viewing window when the wearer is viewing a light source, located at arm's length along the normal line of vision, through said first viewing window.

16. A welding mask as in claims 12 or 13 wherein the included angle between the planes of said tinted lens and said relatively clear lens opening in the direction towards said wearer is in the range of 115°-120°.

17. A welding mask as in claims 1, 2 or 3 in which said relatively transparent lens is mounted beneath said tinted lens.

18. A welding mask as in claims 1, 2 or 3 in which one or more additional relatively transparent lenses adapted for viewing work to be welded, prior to striking an arc, or lighting a torch are mounted adjacent to the bordering edges of the window incorporating said tinted lens, wherein said additional lenses are all angled rearwardly away from the plane of the tinted lens and towards the wearer at an acute angle to the normal line of vision of the wearer through said tinted lens, said angle being sufficient to substantially reduce the amount of light entering into said mask through said second viewing window when the wearer is viewing a light source, located at arm's length along the normal line of vision through said first viewing window.

* * * * *